United States Patent [19]
Krepinsky et al.

[11] Patent Number: 5,977,328
[45] Date of Patent: Nov. 2, 1999

[54] POLYVALENT CARBOHYDRATE MOLECULES

[76] Inventors: Jiri J. Krepinsky, 810 Srigley Avenue, Newmarket, Ontario, Canada, L3Y 1X7; Niculina Lupescu, 5B Heathdale Road, Toronto, Ontario, Canada, M6C 1M

[21] Appl. No.: 08/814,885

[22] Filed: Mar. 12, 1997

[51] Int. Cl.$^6$ .................................................. C08B 31/08
[52] U.S. Cl. .................... 536/18.6; 536/102; 536/111; 536/123; 536/123.13
[58] Field of Search ................................... 536/18.5, 18.6, 536/102, 111, 123, 123.1, 123.13, 124; 426/658

[56] References Cited

U.S. PATENT DOCUMENTS 5,616,698  4/1997  Krepinsky et al. ..................... 536/18.6

OTHER PUBLICATIONS

Köpper et al., *Carbohydrate Research*, vol. 193: 296–302, 1989.
Motawia et al., *Carbohydrate Research*, vol. 277: 109–123, 1995.
*Preparative Carbohydrate Chemistry*, Ed. by Stephen Hanessian, Marcel Dekker, Inc., pp. 283–312, Dec. 1996.
*Monosaccharides: Their Chemistry and Their Roles in Natural Products*, Ed. Collins & Ferrier, John Wiley & Sons, pp. 101–105, 159–163, 468/469, 1995.
Pfannemüller et al., *Carbohydrate Research*, vol. 56: 147–151, 1977.
Haines, A.H, Advances in Carbohydrate Chemistry and Biochemistry (Edited by Tipson & Horton) Academic Press, pp. 13–70, 1981.
Anianson, G. et al., "Anti-adhesive activity of human casein against *Streptococcus pneumoniae* and *Haemophilus influenzae*", *Microbial Pathogenesis*, 1990, 8, 315–323.
Krepinsky, J., "Polymer–Supported Synthesis of Oligosaccharides", Am. Chem. Soc. (Div. Org. Chem.), 212th ACS National Meeting, Orlando, FL, Aug. 25–29, 1996, No. 003.
Liang, R. et al., "Parallel Synthesis and Screening of a Solid Phase Carbohydrate Library", *Science*, 1996, 274, 1520–1522.
Rouhi, A.M., "Oligosaccharides Coming of Age", *Chem. Engin. News*, Sep. 23, 1996, 62–66.
Schmidt, R.R. et al., "Anomeric–Oxygen Activation for Glycoside Synthesis: The Trichloroacetimidate Method", *Carbohydr. Chem. Biochem.*, 1994, 50, 21–123.
Toshima, K. et al., "Recent Progress in O–Glycosylation Methods and Its Application to Natural Products Synthesis", *Chem. Revs.*, 1993, 93, 1503–1531.
Varki, A., "Biological roles of oligosaccharides: all of the theories are correct", *Glycobiology*, 1993, 3(2), 97–130.
Whitfield, D.M. et al., "Glycosylation reactions—present status future directions", *Glycoconjug. J.*, 1996, 13, 5–17.
Zopf, D. et al., "Oligosaccharide anti-infective agents", *Lancet*, 1996, 347, 1017–1020.

*Primary Examiner*—Howard C. Lee
*Attorney, Agent, or Firm*—Woodcock Washburn Kurtz Mackiewicz & Norris, LLP

[57] ABSTRACT

Methods for syntheses of polyvalent carbohydrate molecules by glycosylations of partially protected polysaccharides with a single glycosylating agent or a mixture of glycosylating agents (i.e., a combinatorial library) are disclosed. An alternate method utilizes a glycoside, the aglycon of which carries a halogen which can be under strong alkaline conditions linked with a partially protected polysaccharide by an ether linkage. The product of the latter reaction can be subjected to further glycosylation with a single glycosylating agent or a mixture of such agents (=library). The novel resulting polyvalent carbohydrate molecules may be used as antiinfective agents (antibacterial, antiparasital), both for prevention and treatment of diseases, and as agents either for preventing the formation of, or disrupting, biofilms.

21 Claims, No Drawings

POLYVALENT CARBOHYDRATE MOLECULES

FIELD OF THE INVENTION

This invention relates to the preparation of novel polyvalent carbohydrate molecules, including polyvalent oligosaccharide molecules by linking a carbohydrate or a combinatorial carbohydrate library to a suitable matrix. Combinatorial carbohydrate libraries may be obtained using polymer-supported as well as classical solution methodologies, which may be further transformed into glycosylating agents. The glycosylating agents are then linked to a high-molecular weight matrix to produce, after deprotection, polyvalent hydrocarbon molecules in excellent yields. The matrices do not elicit any immunologic or allergic reactions in human or animal recipients. Such polyvalent molecules prevent infections caused by bacterial colonization, and hence may be used in foods, for example, in infant formulae and young children's foods to decrease the chance of contracting infectious diseases, in oral hygiene products, and in other products, such as disinfectants, cleansers, soaps, deodorants, ear drops and nasal sprays.

The polyvalent carbohydrate molecules may be further used in the treatment of bacterial infections, as they are not expected to cause drug resistance. Furthermore, such carbohydrate polyvalent molecules, by virtue of their strong adherence to sites that bind carbohydrates, will disrupt biofilms or prevent biofilm formation and therefore have applications wherever biofilms are involved.

BACKGROUND OF THE INVENTION

Oligosaccharides occurring naturally in glycolipids, glycoproteins and proteoglycans have been ascribed a variety of functions in biological systems (see Varki, A. *Glycobiology* 3, 97(1993)). Although the universality of these functions is unknown at this point in time, there are properties of oligosaccharides which make them of immediate practical importance because of their possible use as human therapeutics and, particularly important, as preventive agents of human infections. For prevention purposes, these polyvalent carbohydrate molecules can be used as food additives, dental cleansers, mouthwashes, eardrops, ointments, and similar agents. Infections caused by colonization mediated by adherence to tissues through carbohydrate substrate binding are targets of these preventive agents.

As an example, such adherence is the adhesion of pathogens to human epithelia through the binding of pathogens to epithelial cells by bacterial or parasital adhesins. Adhesins are proteins showing specific binding affinity to oligosaccharide (carbohydrate) moieties of glycolipids and glycoproteins displayed on epithelial cells in colonized tissues. Since the attachment to host cells is the initial event of the infectious process, interference with binding by oligosaccharides mimicking the oligosaccharide moieties of glycolipids or glycoproteins prevents (see Zopf, D., Roth, S. *Lancet* 347, 1017 (1996)) or reduces the infection. Such attachment also occurs when the carbohydrate is located on the pathogen and therefore the binding to the host's proteins is mediated by this carbohydrate. Thus carbohydrates naturally occurring in human milk (see Anianson, G., Andersson, B., Lindstedt, R. & Svanborg, C., *Microbial Pathogenesis* 8, 315) offer protection to infants against infections. Carbohydrates may, in addition to protection against infection, be utilized for treatment of infectious diseases that are increasingly more difficult to treat because of growing pathogen resistance to antibiotics and drugs.

Since individual natural oligosaccharides usually bind to their accepting molecules weakly, individual oligosaccharides must be used in impracticably large quantities for an effective treatment. This problem is overcome in carbohydrate polyvalent molecules [see Zopf, D., Roth, S. *Lancet* 347, 1017 (1996)] since such molecules bind the accepting molecules through multiple contacts resulting in strong binding. These polyvalent molecules occupy the carbohydrate binding site tightly and the infectious process is thus interrupted. The combinatorial polyvalent oligosaccharide molecule has a further advantage of making it possible to utilize the strongest binders and their combinations for a particular pathogenic bacterium without any prior knowledge of exact binding requirements of the particular microorganism. The matrix molecule should be a biocompatible material, not eliciting an immune response, suitable for the purpose, for instance a starch for infant foods or a gel-forming oligosaccharide such as a carrageenan for dental pastes, or a similar scaffold for disruption or removal of biofilms. However, all matrices can be considered for all applications. The biofilms are often responsible for infective properties of microorganisms, for failures of implanted bioengineering devices, as well as for malfunctions of engineering structures such as oil pipelines, and the water intakes of municipal water and industrial plants.

DESCRIPTION OF RELATED ART

The polyvalent carbohydrate molecules are defined as glycosylated polysaccharides. Many methods for glycosylation of monosaccharides, oligosaccharides, and other small molecule aglycons are known in the art. The glycosyls should be spread along the polysaccharide chains with an average frequency of no more than one glycosyl per two monosaccharide units of the polymeric chain. The glycosyls are derived from oligosaccharides of general formula [monosaccharide]$_n$, where n=1–5, both linear and branched.

Oligosaccharides have been synthesized (see R. R. Schmidt, W. Kinzy. *Adv. Carbohydr. Chem. Biochem.* 50, 21 (1994); K. Toshima, K. Tatsuta, *Chem. Revs.* 93, 1503 (1993); D. M. Whitfield, S. P. Douglas, *Glycoconjug. J.* 13, 5 (1996); S. H. Khan, R. A. O'Neill, Eds. *Modern Methods of Carbohydrate Synthesis*, Harwood Academic Publishers, (1996)) by solution methodologies for many years, more recently by methods employing enzymes, and by polymer-supported methods, either in solution (see *Oligosaccharides Coming of Age*, Chemical & Engineering News, 62–66, Sep. 23, 1996) or in solid state, and these methods have been described extensively in publications, patents, and reviews. The preparation of oligosaccharide libraries have been recently described using polymer-supported syntheses on polyethylene glycol in grafted copolymers [R-Liang, L. Yan, J. Loebach et al. Science 274, 1520 (1996)] and on polyethylene glycol with dioxyxylyl linker (see U.S. patent application Ser. No. 08/179,096, filed Oct. 1, 1994 to issue Apr. 1, 1997 under U.S. Pat. No. 5,616,698 in the name of Krepinsky et al.). Oligosaccharides or oligosaccharide libraries may be transformed into glycosylating agents by methodologies well known in the art, such as trichloroacetimidates or sulfoxides, by methods described in numerous publications, patents, reviews, and at scientific conferences (see Polymer-Supported Synthesis of Oligosaccharides, J. J. Krepinsky presented at 212$^{th}$ ACS National Meeting, Orlando, Fla., U.S.A., Aug. 25–29, 1996). All of the references cited herein are incorporated herein by reference.

SUMMARY OF THE INVENTION

The present invention provides in one aspect a method for the preparation of polyvalent carbohydrate molecules which comprises:

a) reacting as a first reactant at least one carbohydrate having at least one monosaccharide unit with a second reactant which is a polysaccharide partially protected by protecting groups, and having at least one free hydroxyl group per two consecutive monosaccharide units of polymeric chain, to form a linkage between the free hydroxyl group of the polysaccharide derivative and an anomeric carbon of the carbohydrate;

b) removing the protecting groups; and c) purifying the solid.

The present invention also provides a process for the preparation of polyvalent carbohydrates molecules which comprises the steps of a) forming a glycosylating agent from at least one carbohydrate or a library of carbohydrates equipped with a suitable leaving group at the anomeric carbon of the carbohydrate or a carbohydrate library;

b) subjecting the glycosylating agent to a reaction with a polysaccharide partially protected with acyl protecting groups, the latter being synthesized from the polysaccharide by incomplete acylation or complete acylation and mild incomplete acyl hydrolysis, in which reaction a glycosidic linkage between the glycosylating agent and the partially protected polysaccharide is formed, which linkage cannot be severed under deprotecting conditions;

c) removing all protecting groups; and d) purifying the polyvalent carbohydrate molecules.

Alternatively, a glycosyl can be linked to hydroxyl groups of a polysaccharide through a tether. For example, such a tether may be obtained by a procedure which comprises the steps of a) forming a glycosylating agent from at least one carbohydrate or a library of carbohydrates equipped with a suitable activating leaving group at the anomeric carbon of the carbohydrate or carbohydrate library;

b) subjecting the glycosylating agent to a reaction with a non-geminal hydroxyhalogenoalkane which yields a glycoside of a halogenoalkane;

c) subjecting the glycoside of halogenoalkane to a condensation reaction with a polysaccharide as such, or partially protected, under strong basic conditions, in which reaction an ether linkage between the linker bound to the glycosylating agent and the polysaccharide was formed, which linkage as well as the glycosidic bond cannot be severed during subsequent manipulations;

d) removing all protecting groups;

e) purifying the polyvalent carbohydrate molecules; and, if required f) subjecting such polyvalent molecules to additional glycosylations.

We have now found that glycosylations of matrices partially protected, preferably from 25 to 85% with selected protecting groups can be performed under liquid-phase chemistry conditions adapted to the limited solubility of the matrices. We have also found that suitable partial protection of the matrices such as water-insoluble starch is achieved under acylation conditions using acyl anhydride and the corresponding acid, or in two steps comprising exhaustive protection with acyl protecting groups such as, for example, acetyl groups followed by partial random removal of the protecting groups under the influence of a base. We have further found that the glycosylations are satisfactorily performed in solvents in which the partially protected matrix is soluble, preferably dipolar solvents, and most preferably solvents selected from the group consisting of dioxane, acetonitrile, and dimethylformamide. The progress of glycosylation can be monitored preferably by infrared and N.M.R. spectroscopies and gas-liquid chromatography of acid hydrolysates (alditol acetates) of polyvalent carbohydrate molecules.

These methods make it possible to synthesize novel solid water-soluble polyvalent carbohydrate molecules, the components of which are standard parts of numerous foods. Furthermore, polyvalent carbohydrate molecules are analogous to natural polyvalent glycosylated casein, a known provider of antiinfective protection for newborn and very small children (see Anianson, G., Andersson, B., Lindstedt, R. & Svanborg, C., *Microbial Pathogenesis* 8, 315). The advantage of utilizing polysaccharides as the matrix instead of casein is that polysaccharides are completely devoid of any interference with the recipient's immune system.

These novel polyvalent carbohydrate molecules (PCM) are defined as substances prepared from starch from natural sources using glycosylation reactions and they are characterized by the presence of polymeric chains of the original starch on which carbohydrate molecules are grafted with frequencies of one carbohydrate per two monomer units of the polymer to one carbohydrate unit per fifty monomer units of the polymer. Carbohydrates may be either monosaccharides, single or in any combination, or oligosaccharides, single or in any combination, or a combination of monosaccharides and oligosaccharides. Such polyvalent carbohydrate molecules are water soluble irrespective of whether the original polymer was water soluble or insoluble.

The saccharide may be either an oligosaccharide formed from at least two monosaccharide units by definition, or a monosaccharide. The reducing monosaccharide unit of an oligosaccharide, or a monosaccharide, must be suitably derivatized so as to allow attachment of a leaving group or a derivative thereof. The saccharide must be capable of being elaborated into a substance which is suitable for subsequent glycosylation. The glycosylation is performed under standard liquid-phase chemistry conditions that are well known in the art and are, of course, dependent upon the monosaccharide units and their associated linkages, and upon the nature of protecting groups. The protecting groups are those which would be suitable for the defined purposes and may preferably be selected from $C_2$–$C_7$ acyl groups such as acetyl, ketoacetyl such as levulinyl, branched chain acyls such as pivaloyl, and aromatic acyls such as benzoyl. Such groups may be removed by treatment with basic reagents, and the product purified by precipitation with solvents, preferably certain water-miscible organic solvents. In all other aspects the conditions of reactions performed follow established protocols from solution chemistry. References to these protocols are described earlier. Solution chemistry protocols that may be established in the future, and protocols employing enzymes, will be applicable as well.

Monitoring the glycosylation reaction has been found to be easily achieved, preferably through infrared or N.M.R. spectrometry, or by gas-liquid chromatography of alditol acetates obtained after acid hydrolysis of the product of glycosylation. The deprotection of the product depends on the protecting groups utilized and methods of deprotection are well known in the art. Typically this is achieved by treatment with basic reagents.

The polyvalent carbohydrate molecules may be used in many applications which comprise food components boosting prevention of bacterial infections (e.g., infant formulas and young children's foods), in oral hygiene products, in remedies for illnesses caused by bacterial infections and requiring treatment with less toxic agents than presently available, such as early childhood Otitis media, in products disrupting biofilms or to prevent biofilm formation, in glycotherapeutics for diseases untreatable with conventional means such as cancer, arthritis, and cystic fibrosis. Utilities are not limited to the above applications.

DESCRIPTION OF THE PREFERRED EMBODIMENTS

In order that the invention may be better understood, embodiments will now be described by way of example only, with reference to the accompanying reaction schemes. In one preferred form of the invention, single glycosyl or a library of glycosyls may be randomly (but reproducibly) linked to different polysaccharide hydroxyl groups through glycosidic linkages.

Glycosylation conditions are well known in the art and they may be selected from any of those described in the subsequent examples. Such reactions give good anomeric specificity when glycosylating agents are equipped with a participating group, usually an adjacent functional group that controls the stereochemical outcome of the reaction. Preferred examples of such a participating group include an ester group, such as an acetyl and a benzoyl group, and amidic groups such as acetamido groups. After the reaction is completed, which reaction can be monitored by thin layer chromatography, and then neutralized, the solvent is evaporated in vacuo to dryness and purified by trituration with ethanol to remove residual reagents and solvents from the glycosylated, partially protected polymer. All hydroxyl groups of the glycosylating agents are protected with protecting groups which may preferably be selected from $C_2$–$C_7$ acyl groups such as acetyl, ketoacetyl, such as levulinyl, branched acyl chains such as pivaloyl, and aromatic acyls such as benzoyl. Such groups may be removed by treatment with basic reagents, and purified by precipitation with certain water-miscible organic solvents. In all other aspects the conditions of reactions performed follow established protocols from classical solution chemistry. References to these protocols are described earlier. Solution chemistry protocols that may be established in the future, and protocols employing enzymes, will be applicable as well.

EXAMPLES

The following examples are used to illustrate the present invention. They should not be construed as limiting it in any way. All parts and percentages are by weight unless otherwise indicated. All abbreviations and acronyms have the standard meanings in the art. Following these examples is a set of reaction sequences illustrated by structural formulae. These are identified by corresponding numerical references in the sequences and in the written description.

Example 1
Synthesis of Glycosylated Starch

A polysaccharide (e.g. starch) is partially protected (for instance acylated, e.g. acetylated) to render it soluble in organic solvents so that for subsequent glycosylations methods well known in the art may be utilized, and any other methods equivalent thereto.
Synthesis of Partially Acetylated Starch(1)

A 10% vigorously stirred suspension of commercially available corn starch (0; 1.25 g) in acetic anhydride-acetic acid (1:4.5) was refluxed under atmosphere of argon. The reaction mixture cleared and became noticeably viscous in three hours. The reaction was continued for one more hour and it was quenched by pouring the reaction mixture into water (150 mL) under stirring. The precipitated polysaccharide was allowed to stand at room temperature for 24 hours. The white precipitate was filtered off, washed with distilled water to remove trace acetic acid, with ethanol, and dried at 50° C. in high vacuo to give 1.8 g [34.4% (determined by titration) acetates] of (1). Infrared spectrum in nujol exhibited a strong absorption band at 1738 $cm^{-1}$, a characteristic stretching band of ester carbonyl group, and a hydroxyl absorption band in 3400–3500 $cm^{-1}$ region. This acetylated starch showed sufficient solubility at room temperature in dioxane and N,N-dimethylformamide.
Synthesis of Per-O-acetylated Starch A 10% vigorously stirred suspension of commercially available corn starch (0) (0.5 g) in acetic acid (1:4.5) was refluxed under argon atmosphere. The reaction was continued for 44 hours and it was quenched by pouring the reaction mixture into water (60 mL) under stirring. The precipitated polysaccharide was allowed to leach at room temperature for 24 hours. The precipitate was filtered off, washed with distilled water to remove trace acetic acid, followed by washing with ethanol, and dried at 50° C. in high vacuo to give 0.83 g (92%; 43.75% acetates (determined by titration)). Infrared spectrum in nujol exhibited a strong adsorption band at 1754 $cm^{-1}$, a characteristic stretching band of ester carbonyl groups but no hydroxyl absorption band in the 3400–3500 $cm^{-1}$ region.
Partial Deacetylation of Per-O-acetylated Starch To a solution of per-O-acetylated starch (0.2 g) in dioxane (10 mL) was added aqueous NaOH (1N; 230 $\mu$L) and the cloudy solution was stirred at room temperature for 16 hours. The solution was concentrated to approximately 5 mL, and ethanol (88%; 15 mL) was added at room temperature. The precipitate formed was filtered off, washed with water followed by ethanol, and dried at 50° C. in high vacuo at room temperature. Infrared spectrum (nujol) exhibited absorption at 1746 $cm^{-1}$ (ester carbonyl) and a broader band at 3482 $cm^{-1}$ (hydroxyl group).

Example 2
Synthesis of Lactosyl Starch (3) Using Imidate Method

A mixture of partially acetylated corn starch (1), (300 mg, 1.219 mmol- as diacetyl-1,4 linked glucose residues) and peracetylated lactose trichloroacetimidate (2), (1.427 g, 1.828 mmol) in dry dioxane (15 mL) was stirred at room temperature for 1 hour to ensure that the polymer dissolved completely. Then triethylsilyl triflate (55 $\mu$L, 0.244 mmol) was added dropwise within 5 min. and stirring was continued at room temperature for 3 hours. The reaction was quenched with diisopropylethylamine (100 $\mu$L), and the volatiles were removed in vacuo. The residue was triturated with ethanol (75 mL), the white solid was filtered off, washed with ethanol and dried to yield (3) (614 mg). GC analysis of the deacetylated (3) (cf. Example 5) using the alditol acetates method indicated the presence of one lactose molecule for every 3.2 glucose residues.

Example 3
Synthesis of Lactosyl Starch (5) Using Sulfoxide Method

A suspension of partially acetylated corn starch (82 mg, 0.333 mmol as diacetyl-1,4 linked glucose residues) and peracetylated lactose phenyl sulfoxide (4), (370 mg, 0.497 mmol) in dry dioxane (4.5 mL) was stirred at room temperature for 1 hour. To the resulting solution triflic anhydride (42 $\mu$L, 0.248 mmol) was added and the reaction was stirred at room temperature for 1 hour. Then diisopropylethylamine and four drops of water were added, the volatiles were removed by evaporation, and the residue was triturated with ethanol (20 mL). The solids were filtered off, washed with ethanol and dried to produce (5) (112 mg) as a yellowish white powder. GC analysis of the deacetylated (5) (cf. Example 5) using alditol acetates method indicated the presence of one lactose molecule for every 5.5 glucose residues.

Example 4
Synthesis of Starch Glycosylated with a Library

A mixture of partially acetylated corn starch (1), (200 mg, 0.813 mmol- as diacetylated 1,4 linked glucose residues) and an equimolar mixture of perbenzoylated α-D-mannopyranosyl trichloroacetimidate [(6), 301 mg, 0.406 mmol], perbenzoylated β-D-galactopyranosyl trichloroacetimidate [(7) 301 mg, 0.406 mmol], and perbenzoylated β-D-xylopyranosyl trichloroacetimidate [(8) (246 mg, 0.406 mmol)], (total: 1.218, mmol) in dry dioxane (10 mL) was stirred at room temperature for 1 hour to ensure that the polymer dissolves completely. Then triethylsilyl triflate (37 µL, 0.163 mmol) was added dropwise within 5 min. and stirring was continued at room temperature for 4 hours. The reaction was quenched with diisopropylethylamine (70 µL), and the volatiles were removed in vacuo. The residue was triturated with ethanol (50 mL), the white solid was filtered off, washed with ethanol and dried to yield 9 (253 mg). After deprotection using aq. NaOH (1N), the glycosylated starch was hydrolyzed in aq. trifluroacetic acid (2N) at 110° C. for 2 hours and the reducing monosaccharides were separated and identified by comparison with authentic specimens on a silica gel $G_{60}$ TLC plate (Merck) using ethyl acetate-pyridine-water (10:4:3) as the developing solvent mixture $R_F$: galactose 0.29, glucose 0.35, mannose 0.41, xylose 0.54.

Example 5
Deacetylation of Lactosylated Corn Starch

A suspension of 3 (100 mg) in aqueous sodium hydroxide solution (7.5 mL, pH12.5) was stirred at room temperature for 16 hours. The clear slightly yellow solution was then neutralized with acetic acid to pH 5, and ethanol (30 mL) was added. The precipitate formed was filtered off, washed with ethanol and dried to give a white powder (10), (49 mg). The infrared spectrum in nujol showed no absorption band at 1738 cm−1 thus confirming that all acetates were removed. Solubility in water at room temperature was 10 mg/mL. $^1$H NMR in $D_2O$ (δppm): 4.44 ($J_{1,2}$=7.48 Hz, 1H, H-1, β-galactoside); 4.53 (1 H, H-1), 4.67 ($J_{1,2}$=7.40 Hz, 1 H, H-1), 4.93 ($J_{1,2}$=7.43 Hz, 1H, H-1): the last three signals are of β-glucoside of lactose. Three different signals for β-lactoside reflect a multiplicity of at least three different locations for lactoside.

Example 6
Synthesis of Lactosyl Oxyethyl Starch (12)

The unprotected starch was derivatized in the presence of a strong base with a haloalkyl glycoside, 2-chloroethyl β-per-O-acetylated lactoside (11), prepared as follows: To a solution of peracetylated lactose imidate (1.09 g, 1.4 mmol) and 2-chloroethanol (105 mg, 1,3 mmol) in dry dichloromethane (10 mL) cooled to 0° C. was added $BF_3.Et_2O$ (40 mg, 0.28 mmol). The cooling bath was removed, the reaction temperature was allowed to rise, and the reaction mixture was stirred for two hours at room temperature. Diisopropylethylamine was added to neutrality, the volatiles were removed by evaporation in vacuo and the residue was dissolved in dichloromethane and subjected to chromatography on a silica gel column (80 g, 2% MeOH in $CH_2Cl_2$). Peracetylated lactoside (11) was eluted in early fractions (683 mg, 75%).

The derivatization of starch was performed as follows: To a solution of dry corn starch (50 mg, 0.308 mmol as 1–4 linked glucose residues) in 50% aqueous NaOH (0.7 mL) was added acetone (1 mL) and solid (11) (240 mg, 0.343 mmol). The reaction mixture was refluxed for 16 hours. Acetone was removed in vacuo and the remaining solution was diluted with distilled water to 2 mL and neutralized to pH 7 with AcOH. The addition of EtOH (6 mL) precipitated 12 (54 mg). Gas liquid chromatography of alditol acetates methods indicated a frequency of one lactose per 47 glucose residues.

Example 7
Gas-Liquid Chromatography of Alditol Acetates

Reducing sugars obtained after acid hydrolysis (2 M trifluoroacetic acid, 2 h at 100° C.) were quantified by conversion to alditol acetates, which were prepared as described (Albersheim, P., Nevins, D. J., English, P. D., Karr, A. Carbohydr. Res. 5, 340 (1967) except that Dowex 50×8 ($H^+$) was used to neutralize the excess of $NaBH_4$. The samples were analyzed on a fused silica capillary column AT-225, 15 m×0.53 mm i.d. (Altech) with a Varian 3400 gas chromatograph coupled to a HP-3396 Integrator. The following oven temperature program was used: an initial temperature of 130° C. for 10 min, followed by an increase at a rate of 2° C. min$^{-1}$ to 240° C., which temperature was maintained for 10 min. The injector and detector temperatures were maintained at 250° C., using helium as the carrier gas: flow rate 10 mL min. The per-O-acetylated alditols were injected using the splitless mode and were detected with a flame-ionization detector. The ratios of per-O-acetylated-glucitol to per-O-acetylated-galactitol were used to calculate the degree of lactosylation.

Those skilled in the art will recognize that many modifications and variations of the present invention are possible in light of the above teachings. It is therefore to be understood that, within the scope of the appended claims, the invention may be practiced otherwise than as specifically described.

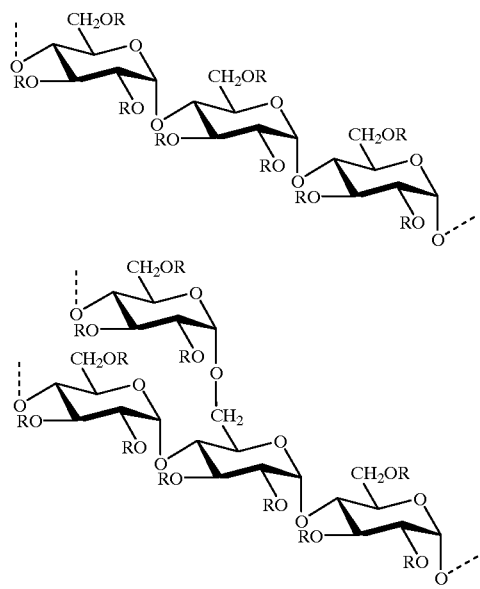

-continued

0: R = H (two forms of starch)
1: R = H or Ac (random distribution)
5: & 3: R = H and Ac and where $R_1$ = Ac 10: R, $R_1$ = H in 5 or 3

12: R = H and

2: $R_1$ = —O—C(=NH)—CCl$_3$
4: $R_1$ = —O—S(=O)—C$_6$H$_5$
11: $R_1$ = —OCH$_2$CH$_2$Cl 6, 7, 8

We claim:

1. A method for the preparation of polyvalent carbohydrate molecules which comprises:
   a) reacting, as a first reactant, at least one carbohydrate having at least one monosaccharide unit with a second reactant, which is a partially protected starch having at least one free hydroxyl group per two consecutive monosaccharide units of the starch, to form a linkage between free hydroxyl groups of the partially protected starch and the anomeric carbon of the carbohydrate;
   b) removing the protecting groups; and
   c) purifying the formed polyvalent carbohydrate molecule.

2. The method of claim 1 wherein the carbohydrate is a monosaccharide or a mixture of monosaccharides.

3. The method of claim 1 wherein the carbohydrate is an oligosaccharide or a mixture of oligosaccharides.

4. The method of claim 1 wherein the carbohydrate is a mixture of monosaccharides and oligosaccharides.

5. The method of claim 1 wherein the protecting groups are acyl groups.

6. The method of claim 1 wherein the protecting groups are $C_2$–$C_7$ acyl groups.

7. The method of claim 1 wherein the protecting groups are selected from acetyl, levulinyl, pivaloyl and benzoyl groups.

8. The method of claim 1 wherein the carbohydrate comprises a glycosyl trichloroacetimidate.

9. The method of claim 1 wherein the carbohydrate comprises a glycosyl sulfoxide.

10. The method of claim 1 wherein the purification step comprises recrystallization.

11. The method of claim 1 wherein the reaction for completion is monitored by infrared spectroscopy, N.M.R. spectroscopy and/or by gas-liquid chromatography of alditol acetates.

12. The method of claim 1 wherein the linkage between the free hydroxyl groups of the starch derivative and the anomeric carbon of the carbohydrate is through a tether obtained by:
    a) forming a glycosylating agent from at least one carbohydrate molecule or a library of carbohydrate molecules equipped with a suitable activated leaving group at the anomeric carbon of the carbohydrate molecule or library of carbohydrate molecules;
    b) subjecting the glycosylating agent to a reaction with a non-geminal hydroxylhalogenoalkane which yields a tethered first reactant which comprises of a glycoside of a halogenoalkane.

13. The method of claim 12 wherein the carbohydrate is a monosaccharide or a mixture of monosaccharides.

14. The method of claim 12 wherein the carbohydrate is an oligosaccharide or a mixture of oligosaccharides.

15. The method of claim 12 wherein the carbohydrate is a mixture of monosaccharides and oligosaccharides.

16. The method of claim 12 wherein the protecting groups are acyl groups.

17. The method of claim 12 wherein the protecting groups are $C_2$–$C_7$ acyl groups.

18. The method of claim 12 wherein the protecting groups are selected from acetyl, levulinyl, pivaloyl and benzoyl groups.

19. The method of claim 12 wherein the glycosylating agent comprises a glycosyl trichloroacetimidate.

20. The method of claim 12 wherein the glycosylating agent comprises a glycosyl sulfoxide.

21. A water soluble polyvalent carbohydrate molecule comprising of a starch derivative in which a carbohydrate selected from the group consisting of a monosaccharide or a mixture of monosaccharides; an oligosaccharide or a mixture of oligosaccharides; and a mixture of monosaccharides and oligosaccharides is grafted via a linkage between the free hydroxyl groups of a starch and the anomeric carbon of the carbohydrate with a frequency of one carbohydrate per two to fifty monomer units of the starch.

* * * * *